United States Patent
Shah et al.

(10) Patent No.: US 11,636,750 B2
(45) Date of Patent: Apr. 25, 2023

(54) VISIBLE RANGE DETECTION SYSTEM

(71) Applicant: BAKER ENGINEERING & RISK CONSULTANTS, INC, San Antonio, TX (US)

(72) Inventors: Jatin Navin Shah, Eden Prairie, MN (US); Murtaza Ibrahimbhai Gandhi, Katy, TX (US); John Moosemiller, San Antonio, TX (US); William A. Mather, Katy, TX (US)

(73) Assignee: BAKER ENGINEERING & RISK CONSULTANTS, INC., San Antonio, TX (US)

( * ) Notice: Subject to any disclaimer, the term of this patent is extended or adjusted under 35 U.S.C. 154(b) by 273 days.

(21) Appl. No.: 17/062,466

(22) Filed: Oct. 2, 2020

(65) Prior Publication Data
US 2021/0104144 A1 Apr. 8, 2021

Related U.S. Application Data (60) Provisional application No. 62/911,058, filed on Oct. 4, 2019.

(51) Int. Cl.
*G08B 21/12* (2006.01)
*H04N 13/239* (2018.01)
(Continued)

(52) U.S. Cl.
CPC ........ *G08B 21/12* (2013.01); *G01N 21/3504* (2013.01); *G01N 21/39* (2013.01);
(Continued)

(58) Field of Classification Search
CPC ........ G08B 21/12; G08B 21/14; G08B 21/16; G01N 21/3504; G01N 21/39;
(Continued)

(56) References Cited

U.S. PATENT DOCUMENTS

| | | | | |
|---|---|---|---|---|
| 2008/0155241 A1* | 6/2008 | Varku | ................ | G05B 19/0423 713/1 |
| 2011/0186657 A1* | 8/2011 | Haviland | .............. | F41B 9/0087 239/722 |

(Continued)

OTHER PUBLICATIONS

Husky Energy Inc. (2019) "Superior Refinery Rebuild-HF FAQs," Retrieved from URL https://huskyenergy.com/superior/hydrogen-fluoride-faqs.asp.

*Primary Examiner* — Stephen P Coleman
(74) *Attorney, Agent, or Firm* — McDermott Will & Emery LLP (57) ABSTRACT

A chemical release detection system includes a camera, an output control member, a mitigation member, and a controller in operative communication with the camera, the output control member, and the mitigation member. The camera is configured to detect a chemical release. The output control member is configured to generate commands. The mitigation member is configured to reduce risk generated by the chemical release based on the commands by the output control member. The controller is configured to notify a user of the chemical release, and provide an origin of the release and a direction of the release. The controller controls the operation of the output control member and the mitigation member.

9 Claims, 7 Drawing Sheets

(51) Int. Cl.
*G06T 7/70* (2017.01)
*G06T 7/00* (2017.01)
*G01N 21/39* (2006.01)
*G01N 33/00* (2006.01)
*G01N 21/3504* (2014.01)
*G06V 40/16* (2022.01)
*G01N 27/416* (2006.01)

(52) U.S. Cl.
CPC ....... *G01N 33/0054* (2013.01); *G06T 7/0004* (2013.01); *G06T 7/70* (2017.01); *G06T 7/97* (2017.01); *G06V 40/161* (2022.01); *H04N 13/239* (2018.05); *G01N 27/4162* (2013.01); *G01N 2201/06113* (2013.01); *G06T 2207/30108* (2013.01); *G06T 2207/30201* (2013.01)

(58) Field of Classification Search
CPC ........... G01N 33/0054; G01N 27/4162; G01N 2201/06113; G06T 7/0004; G06T 7/70; G06T 7/97; G06T 2207/30108; G06T 2207/30201; G06V 40/161; H04N 13/239; H04N 5/232; H04N 5/247; G01M 3/04; G01M 3/38; Y02A 50/20
USPC ........................................................ 382/103
See application file for complete search history.

(56) References Cited

U.S. PATENT DOCUMENTS

| | | | | |
|---|---|---|---|---|
| 2012/0107173 | A1* | 5/2012 | Sengupta | F42B 12/50 422/292 |
| 2013/0191681 | A1* | 7/2013 | Moiseev | G05B 9/03 714/2 |
| 2014/0020763 | A1* | 1/2014 | Phlegm | G01M 3/16 137/467.5 |
| 2016/0295089 | A1* | 10/2016 | Farahani | H04N 5/247 |
| 2017/0089800 | A1* | 3/2017 | Huseynov | G01S 5/20 |
| 2018/0292286 | A1* | 10/2018 | Dittberner | G08G 5/0039 |
| 2019/0285019 | A1* | 9/2019 | Dudar | F02D 41/0007 |
| 2020/0302352 | A1* | 9/2020 | Hubbard | G05B 15/02 |

\* cited by examiner

VISIBLE RANGE DETECTION SYSTEM

RELATED APPLICATION

This application claims priority to U.S. Provisional Application No. 62/911,058 filed on Oct. 4, 2019, the entire disclosure of which is incorporated herein by reference.

FIELD OF THE INVENTION

The present invention relates to a chemical detection system and more particularly to a chemical release detection system for chemicals such as hydrofluoric acid (HF), ammonia ($NH_3$), and other flammable/toxic gases that can be detected in the visual spectrum.

BACKGROUND

With increased usage of chemicals such as hydrofluoric acid (HF), ammonia ($NH_3$), and other flammable/toxic chemicals in manufacturing facilities, chemical processing operations must consider and prepare for accidental release of the flammable/toxic chemicals from pressurized storage tanks and/or pipe lines. In particular, a reliable detection mechanism to monitor, detect and respond to HF, $NH_3$, or other gases is desirable. Current hydrofluoric acid (HF), ammonia ($NH_3$) and/or flammable/toxic gas detections are generally performed by using application specific detectors for each chemical such as for example, point and laser type open path detectors. As such, the chemical processing operations require many detectors to be properly placed and spaced for each chemical to be detected. However, when chemicals are processed in a large area or large quantities, unique challenges in the detection process are presented. For example, even though multiple detectors may detect the release, they may not necessarily send a warning to a risk management/recovery team, including such critical information as the origin and direction of the released chemical. Moreover, when such a release of flammable/toxic chemical occurs, the flammable/toxic chemical must be managed in a timely and reliable manner. A flammable/toxic chemical release must be isolated and/or controlled to reduce the risk associated with the released chemicals.

Therefore, there exists a need for a responsive chemical monitor/detection system that monitors, effectively detects and, if a chemical release occurs: 1) sends a warning to the risk management/recovery team with critical information, such as the point of origin of the chemical release and the direction of the released chemical, 2) activates an isolation process for the released chemical, and 3) activates a mitigation process to lower the risk of exposure, and to further prevent damage by the released chemical. Such a system should operate with little human intervention, and be capable of effectively communicating between the various components thereof.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

It is to be understood that the following disclosure provides many different embodiments, or examples, for implementing different features of the disclosure. Specific embodiments or examples of components and arrangements are described below to simplify the present disclosure. These are, of course, merely examples and are not intended to be limiting. For example, dimensions of elements are not limited to the disclosed range or values, but may depend upon process conditions and/or desired properties of the device. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (rotated 90 degrees or at other orientations) and the spatially relative descriptors used herein may likewise be interpreted accordingly. In addition, the term "made of" may mean either "comprising" or "consisting of."

In some embodiments, the chemicals being monitored are flammable or toxic gases (flammable/toxic gases) including, for example, hydrofluoric acid (HF) and ammonia ($NH_3$). In general, when a flammable/toxic gas is released, the flammable/toxic gas has to be quickly isolated to reduce the risk of injury to people or damage to equipment. Embodiments of the disclosure contain and ultimately remove the released flammable/toxic gases from the affected area using mitigation and/or safety processes according to the disclosure. This system is particularly useful for flammable/toxic gases used in the chemical processing industry, but is not limited to such industry.

Cameras can be used to detect the release of flammable/toxic gases when the flammable/toxic gas creates a visible indicator of its release, such as by forming a cloud. However, the use of typical visual range cameras can be limited by the location of the camera, including the height and angle; and/or the verification process that require human intervention, including interpreting the visual data, determining the direction of the gas release, and providing instructions for dealing with the gas release. In some cases, human intervention requires a chemical process to be shut down and re-started, which results in an extended recovery time and high costs during lengthy downtimes. The recovery time and costs can be reduced if the mitigation team is provided with information such as: 1) where the chemical release originated and 2) the direction in which the chemical release is spreading. Previously, in many cases, this was not determined until the chemical release already had unacceptably expanded.

Moreover, communication between a central processor and the risk mitigation device was limited in prior systems. This lack of communication made it difficult to determine the risk mitigation processes and/or predict necessary remediation actions such as, for example, when a water mitigation equipment needed to be activated or adjusted.

In cases where water mitigation equipment was used, water cannons may not have been pointed in the direction towards the gas release and/or may not have been turned on simultaneously, thereby resulting in excessive water use, low scrubbing efficiency, and an ineffective mitigation of the gas cloud, and resulting in further delay of the recovery process. Further still, the lack of communication made it difficult for needed adjustments, modifications or updates to the mitigation process or the affected device/equipment before people were injured or equipment was damaged. This resulted in a significant recovery time and/or process for the containment of the released gases and/or downtime of the chemical processing system.

Figure 1:
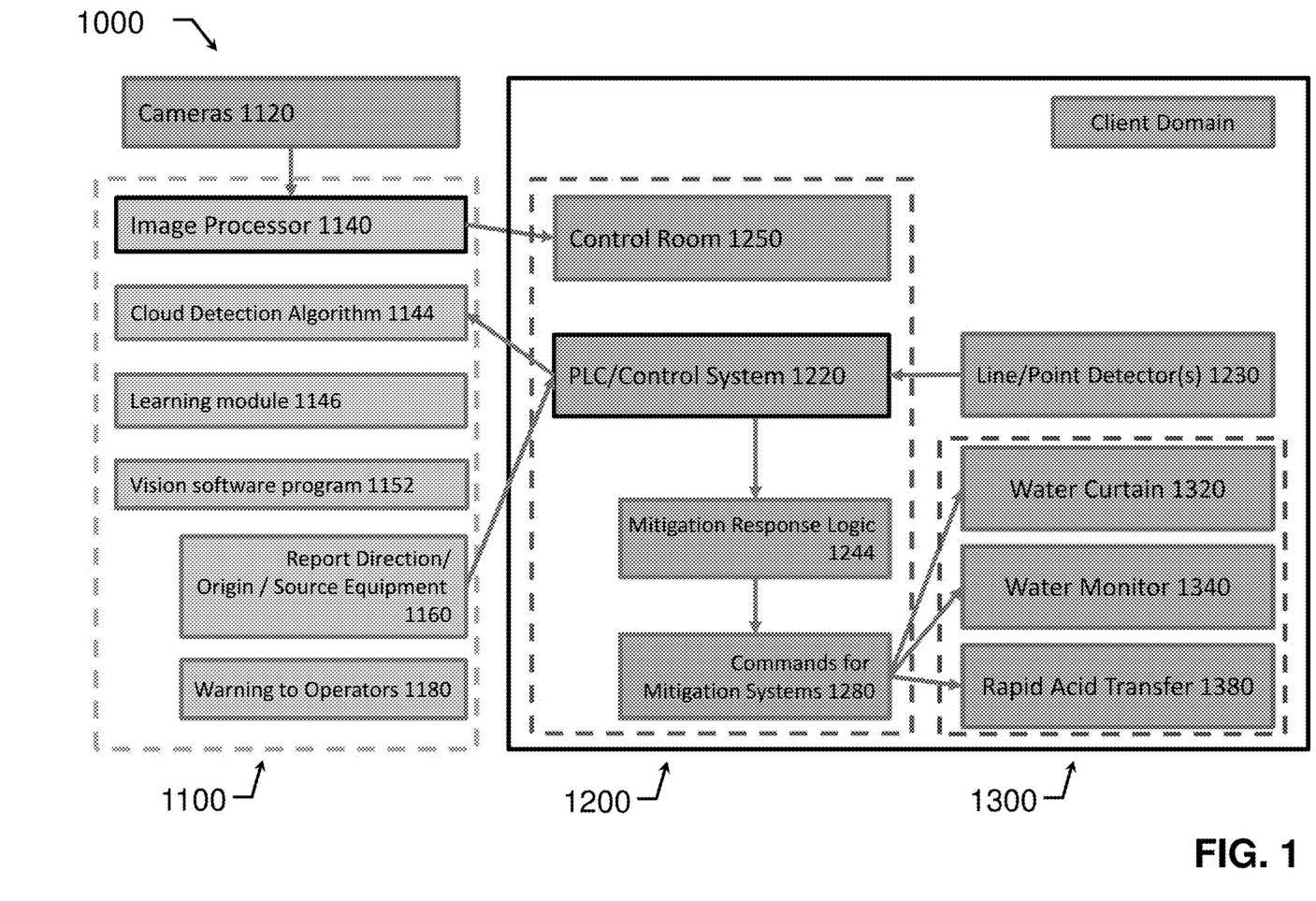
FIG. 1 shows a chemical release detection system according to an embodiment of the disclosure.

Referring to FIG. 1, an embodiment of a chemical release detection system 1000 is shown. The chemical release detection system 1000 includes a monitoring/processing member 1100, an output control member 1200, and an isolation/mitigation member 1300.

Figure 2:
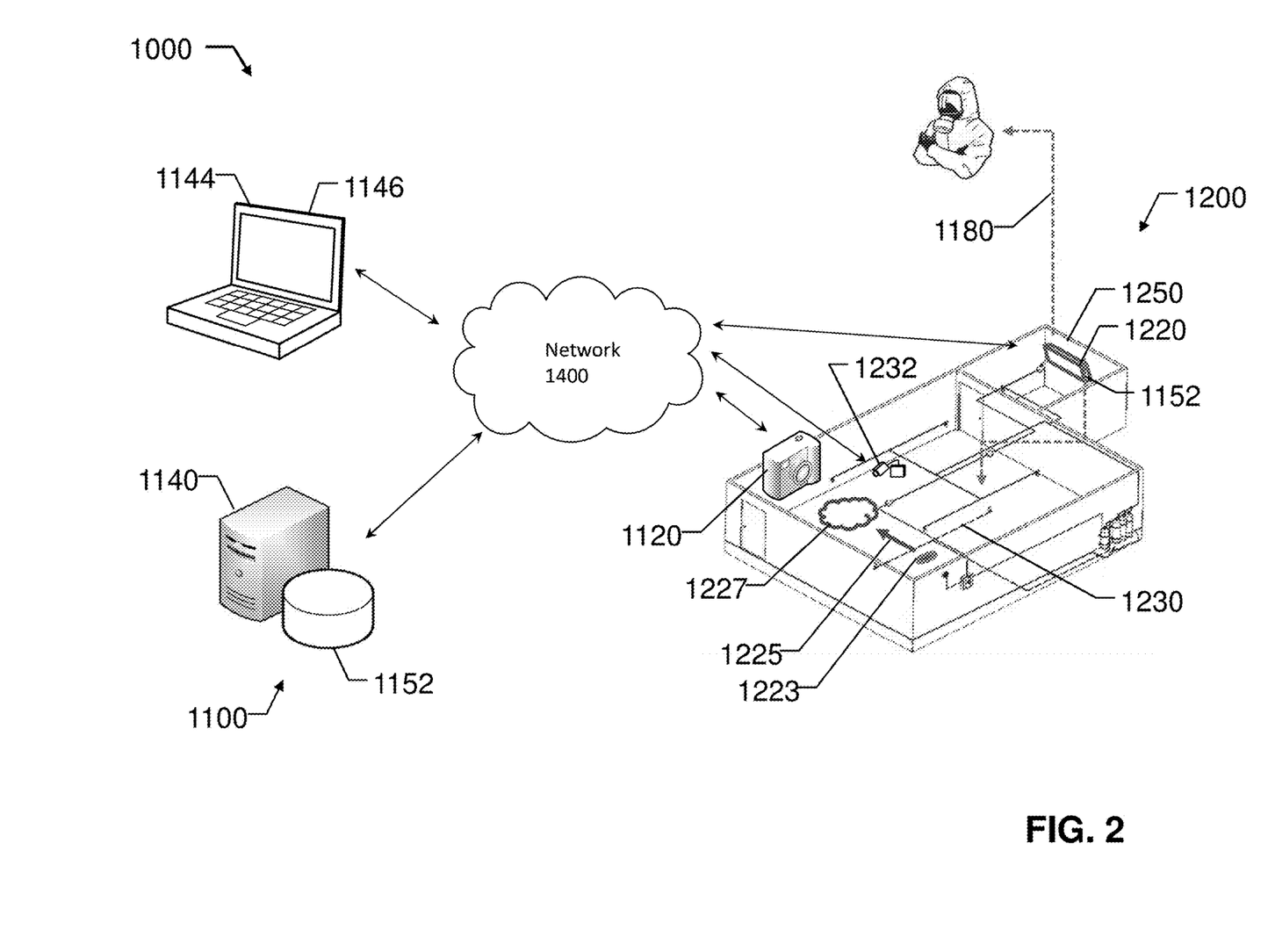
FIG. 2 schematically illustrates an exemplary chemical release detection system according to some embodiments of this disclosure.

As also shown in FIG. 2, the monitoring/processing member 1100 may include a plurality of visual range cameras 1120 and an image processor 1140. The monitoring/processing member 1100 may be composed of several components that monitor and detect a release of the chemical from the targeted area and determine whether it exceeds a pre-established safety threshold for the release. Gases such as HF and $NH_3$ form visible clouds when they are released in air. Therefore, a plurality of visual range cameras 1120 that operate in the visible spectrum are used. The cameras support Gig E/other standard protocols in some embodiments. The plurality of visual range cameras 1120 are located at different places in the chemical processing area and are configured for different fields of view (FOV) to cover the targeted unit/area of concern in some embodiments. The plurality of visual range cameras 1120 may be configured to triangulate an origin and a direction of the release. The plurality of visual range cameras 1120 may be configured to operate in low light conditions and are protected against wind/weather conditions.

By way of a further non-limiting example, the plurality of visual range cameras 1120 provide image data to the image processor 1140 to determine the origin 1223 and direction 1225 of the release. The plurality of visual range cameras 1120 may take images of a gas cloud 1227 created by a flammable/toxic gas as it passes within a field of view of the cameras. The plurality of visual range cameras 1120 may be any appropriate camera, including a high-speed digital camera, a security camera, a DSLR camera, a video camera, etc. The image processor 1140 may include a software program having one or more control algorithms in operative communication with the plurality of visual range cameras 1120.

The image processor 1140 and plurality of visual range cameras 1120 may be wireless or directly connected in any appropriate manner (e.g., WI-FI, Ethernet, NFC, ZigBee, etc.). The plurality of visual range cameras 1120 may include the following job/program memory of a 512 MB non-volatile flash memory and/or unlimited storage via a remote network device, including, without limitation a computing device. The plurality of visual range cameras 1120 may include an image processor and memory. The plurality of visual range cameras 1120 may include a ⅔-inch charge coupled device (CCD) and a global shutter. The plurality of visual range cameras may be used with the global shutter to accumulate images with the exposure starting and ending at the same time. At the end of the exposure time, the images are read out simultaneously. As a result, the image using the global shutter would have less motion blur of the moving objects than the image using a rolling shutter. In an alternative embodiment, the plurality of visual range cameras may be used with the rolling shutter. The cameras 1120 may have a resolution (pixels) of 1024×768 and a recording speed of 5 or more full frames per second. The cameras 1120 may include a c-mount lens type and may include discrete inputs of an opto-isolated, acquisition trigger input. Additional inputs available may include a compatible input/output (I/O) module and/or unlimited inputs when using an Ethernet I/O system. The discrete outputs may include two built-in, high-speed outputs. Additional outputs may be available such as a compatible I/O module and unlimited outputs when using an Ethernet I/O system.

The image processor 1140 may include a software program having one or more cloud detection algorithms 1144. The one or more cloud detection algorithms 1144 may include a learning module 1146 based on the characteristics of the gas cloud 1227 to discern between nuisance releases (e.g. steam and compressed air) and flammable/toxic releases. The learning module 1146 may be explicitly or implicitly trained to learn, determine or infer the gas cloud 1227 that achieve current and/or anticipated isolation/mitigation requirements. The one or more cloud detection algorithms 1144 may also include a method to determine certainty values for various releases, which then can be combined to use signals from $HF/NH_3$ gas detectors 1232 and other flammable/toxic gas detectors to verify a release. In some embodiments, the gas detectors 1232 include electrochemical gas sensors or infrared gas detectors that identify the chemical composition of the gas release. The one or more cloud detection algorithms 1144 may be further configured to digitally zoom to the released chemical origin and provide a visual overlay to help an operator and the risk management/recovery personnel to determine further mitigation action plans. The one or more cloud detection algorithms 1144 may be further configured to record and review video of the release for a time period before the release starts until the release stops.

The one or more cloud detection algorithms 1144 are configured to monitor and detect the origin and the direction of the release for the gas cloud 1227, including the chemical composition, the size, shape, or other characteristics of the flammable/toxic gas to determine an appropriate safety response. The software program may, by way of a non-limiting example, analyze pixel patterns using these programmed algorithms 1144 to check for the released chemical. This feature is particularly useful to determine when and when the chemical release originated from. Additionally, the software program may serve to provide an enlarged visual representation of the chemical in question for analysis of the direction of the cloud 1227 of released gas. The one or more cloud detection algorithms 1144 may further aid in the photographing of the flammable/toxic gas, enhancement of the image such as contrasting the area of the flammable/toxic gas. This provides a more accurate image of the released chemical and the released area/location in some embodiments. The one or more cloud detection algorithms 1144 may include any appropriate light source, including, but not limited to, a dark field ring light, a black light, an incandescent light bulb, LED, etc. Further, any image enhancing device may be utilized with the present disclosure. The chemical release detection system 1000 may also contemplate a computing device and/or software program that provides enhancements to the images taken, such as post processing of the image. In some embodiments, the images are not enhanced, i.e. the plurality of visual range cameras 1120 have a sufficient resolution that such enhancements are not necessary. In other embodiments, an image enhancement, such as those described herein, are utilized on all of the images, some of the images (such as ones that exceed a specific threshold), or on a random or select number of the images.

In some embodiments, the chemical release detection system includes one or more gas detectors 1232 including, electrochemical gas sensors or laser spectroscopic detectors. The laser spectroscopic detectors 1232 may be tunable to specific wavelengths to identify the chemical composition of the released gas. In some embodiments, the laser spectroscopic detector 1232 detects infrared wavelengths, but the detectors are not limited to infrared detectors. In some embodiments, the laser spectroscopic detectors 1232 are configured to measure spectral changes at each pixel of an image and look for specific spectral signatures that indicate the presence of target gases. Because the gas cloud of chemicals such as hydrofluoric acid (HF), ammonia ($NH_3$), may look similar to steam clouds, using the gas detectors 1232, such as laser spectroscopic detectors or electrochemical sensors may verify the presence of a toxic/flammable gas release. In some embodiments, the detection of a toxic/flammable gas triggers the cameras to further identify information such as: 1) where the chemical release originated from and 2) the direction in which the chemical release is spreading.

As shown in FIG. 2, the output control member 1200 of the chemical release detection system 1000 is connected to a network 1400 through a network interface. The network 1400 can be a part of a network of computers (for example, a LAN, a WAN, or an Intranet, or a network of networks, for example, the Internet).

The images and/or recorded video may be routed to a control room 1250 for further analysis. A vision software program 1152 that analyzes images, recorded video, and other pertinent information about the flammable/toxic gas cloud 1227 may be run in the control room 1250. Images may also be enhanced in the control room. In some embodiments, the control room 1250 is used as a communication hub between the various components of the system.

The output control member 1200 of the chemical release detection system 1000 may include a programmable logic controller (PLC)/control device 1220. The PLC/control device 1220 receives signals from line/point detectors 1230 and transmits a running cloud detection algorithm 1144 to the image processor 1140. The PLC/control device 1220 or other controllers are configured to generate outputs (deluge system, water curtain and others), an alarm, and provide a visual view of the cloud 1227 to operators in the control room 1250. The PLC/control device 1220 may include a relay with dry contact outputs to activate an alarm and/or mitigation systems.

The PLC/control device 1220 further sends a warning 1180 to the risk management/recovery team for further risk mitigation processes in some embodiments. Through feedback loops, the chemical release detection system 1000 can provide instantaneous warnings to the risk management/recovery team as well as the emergency response team, and the like. The delivery of feedback via text message, email or other forms of communication allows an efficient communication/response among the risk management/recovery team. In some embodiments, the delivery of the feedback may be coupled with an automatic control/adjustment to the corresponding equipment without human instruction or human intervention. In some embodiments, this involves adjusting the parameters or settings on the chemical process lines. In other embodiments, the monitoring/processing member 1100 reroutes the chemical process line. In particular embodiments, the monitoring/processing member 1100 shuts down a portion of the chemical processing line. Shutting down the processing line may allow for evacuation of the chemical processing plant or a portion of the plant.

Figure 3:
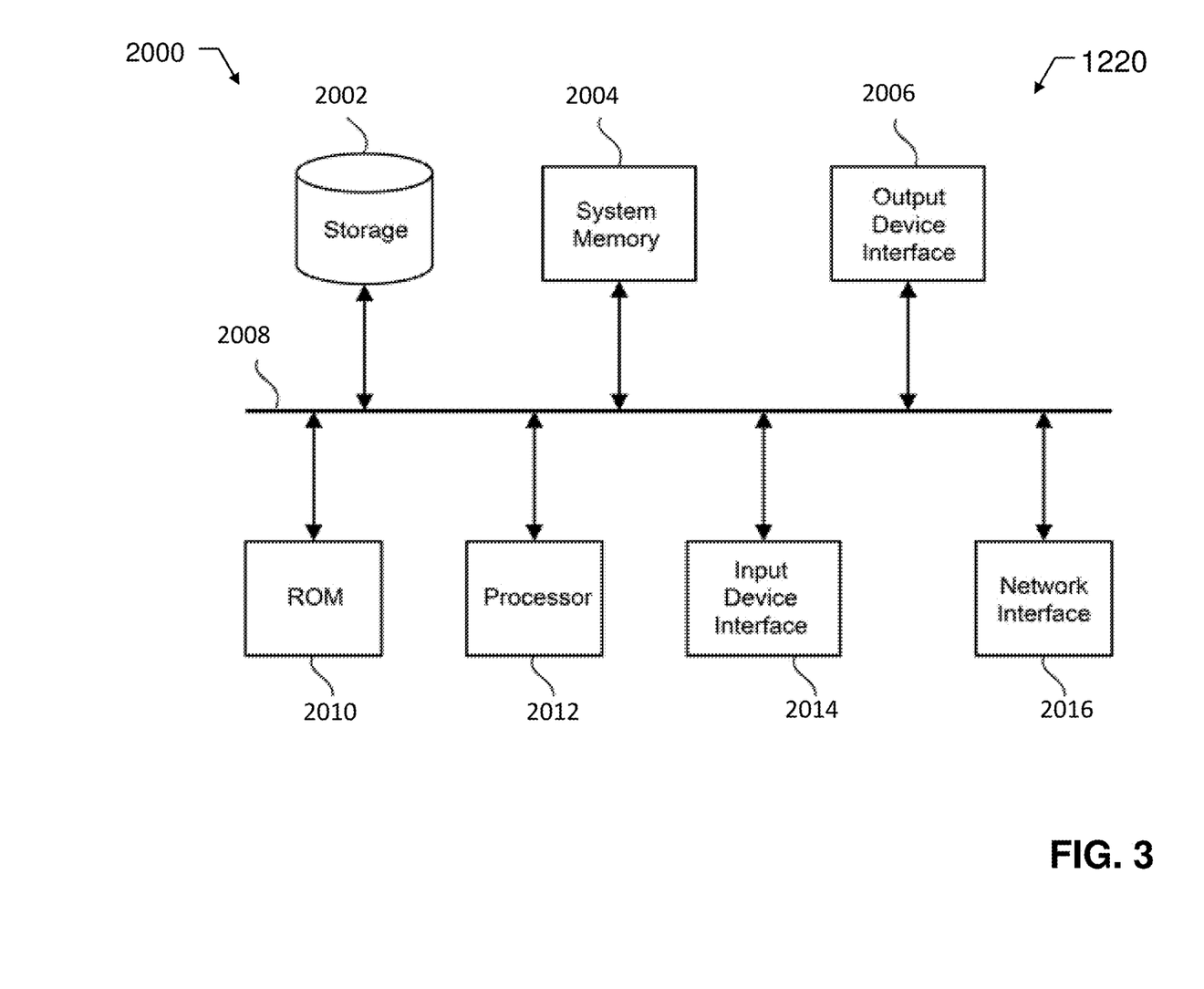
FIG. 3 schematically illustrates a controller in accordance with some embodiments of the disclosure.

FIG. 3 schematically illustrates an exemplary electronic system 2000 in which some embodiments of the PLC/control device 1220 can be implemented. In one or more embodiments, the PLC/control device 1220 may be, or may include all or part of, the electronic system components that are discussed below with respect to the electronic system 2000. The electronic system 2000 can be a computer, phone, or any other sort of electronic device. Such an electronic system includes various types of computer readable media and interfaces for various other types of computer readable media. The electronic system 2000 includes a bus 2008, processor(s) 2012, a system memory 2004, a read-only memory (ROM) 2010, a permanent storage device 2002, an input device interface 2014, an output device interface 2006, and a network interface 2016. The bus 2008 collectively represents all system, peripheral, and chipset buses that communicatively connect the numerous internal devices of the electronic system 2000. For instance, the bus 2008 communicatively connects the processor(s) 2012 with the ROM 2010, system memory 2004, and permanent storage device 2002.

From these various memory units, the processor(s) 2012 retrieves instructions to execute and data to process in order to execute the processes of the subject disclosure. The processor(s) can be a single processor or a multi-core processor in different implementations.

The ROM 2010 stores static data and instructions that are needed by the processor(s) 2012 and other modules of the electronic system. The permanent storage device 2002, on the other hand, is a read-and-write memory device. This device is a non-volatile memory unit that stores instructions and data even when the electronic system 2000 is off. Some embodiments of the subject disclosure use a mass-storage device (for example, a magnetic or optical disk, or flash memory) as the permanent storage device 2002.

Other implementations use a removable storage device (for example, a floppy disk, flash drive) as the permanent storage device 2002. Like the permanent storage device 2002, the system memory 2004 is a read-and-write memory device. However, unlike the storage device 2002, the system memory 2004 is a volatile read-and-write memory, such as a random access memory. The system memory 2004 stores some of the instructions and data that the processor needs at runtime. In some embodiments, the processes of the subject disclosure are stored in the system memory 2004, the permanent storage device 2002, or the ROM 2010. For example, the various memory units include instructions for displaying graphical elements and identifiers associated with respective applications, receiving a predetermined user input to display visual representations of shortcuts associated with respective applications, and displaying the visual representations of shortcuts. From these various memory units, the processor(s) 2012 retrieves instructions to execute and data to process in order to execute the processes of some embodiments.

The bus 2008 also connects to the input and output device interfaces 2014 and 2006. The input device interface 2014 enables the user to communicate information and select commands to the electronic system. Input devices used with the input device interface 2014 include, for example, alphanumeric keyboards and pointing devices (also called "cursor control devices"). The output device interface 2006 enables, for example, the display of images generated by the electronic system 2000. Output devices used with the output device interface 2006 include, for example, printers and display devices, for example, cathode ray tubes (CRT) or liquid crystal displays (LCD). Some embodiments include devices, for example, a touchscreen that functions as both an input and an output device.

As shown in FIG. 3, the bus 2008 also couples the electronic system 2000 to a network (shown in FIG. 2) through a network interface. In this manner, the computer can be a part of a network of computers (for example, a LAN, a WAN, or an Intranet, or a network of networks, for example, the Internet). Any or all components of the electronic system 2000 can be used in conjunction with the subject disclosure.

Figure 4A:
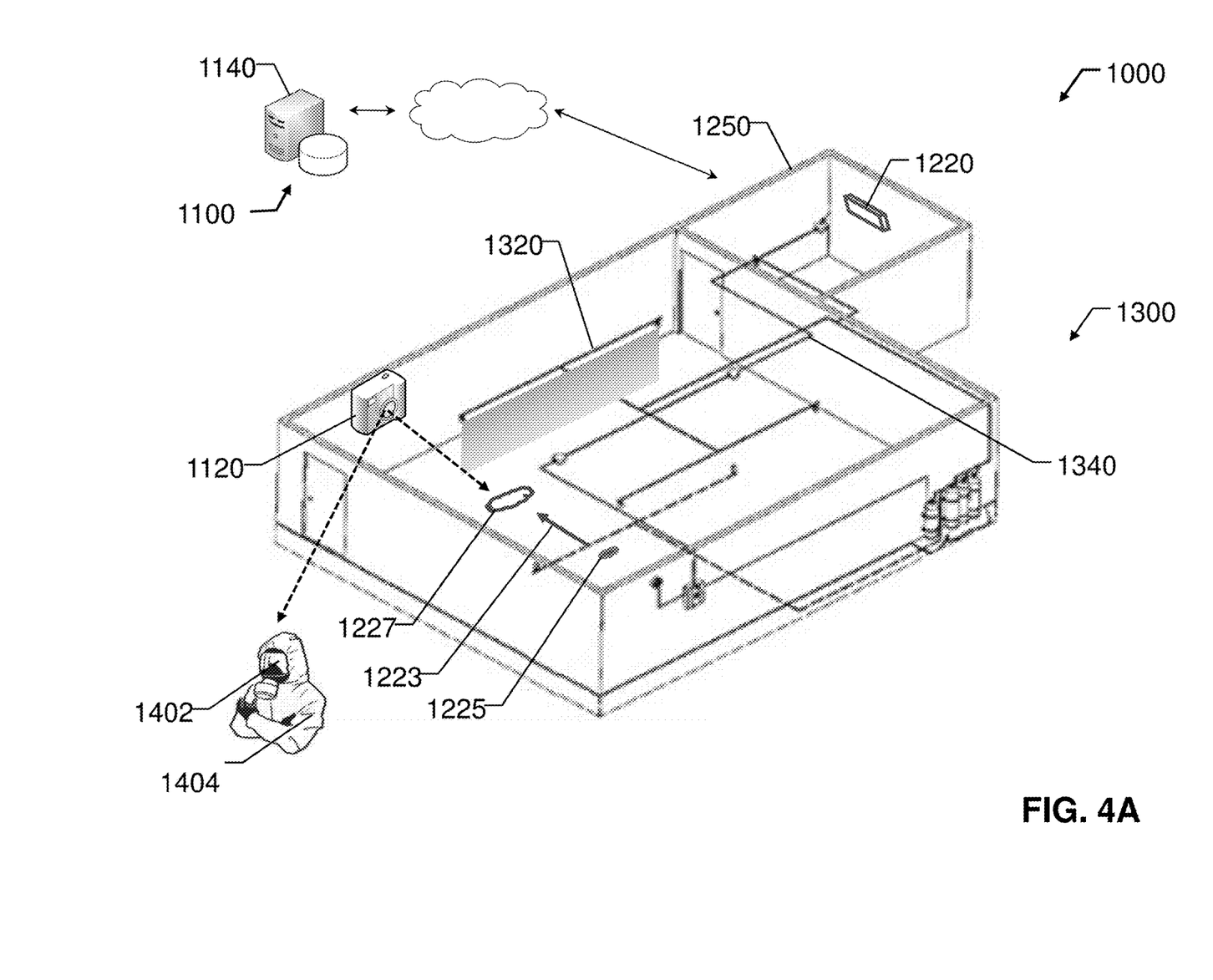
FIGS. 4A and 4B schematically illustrate another exemplary chemical release detection system according to some embodiments of this disclosure.
Figure 4B:
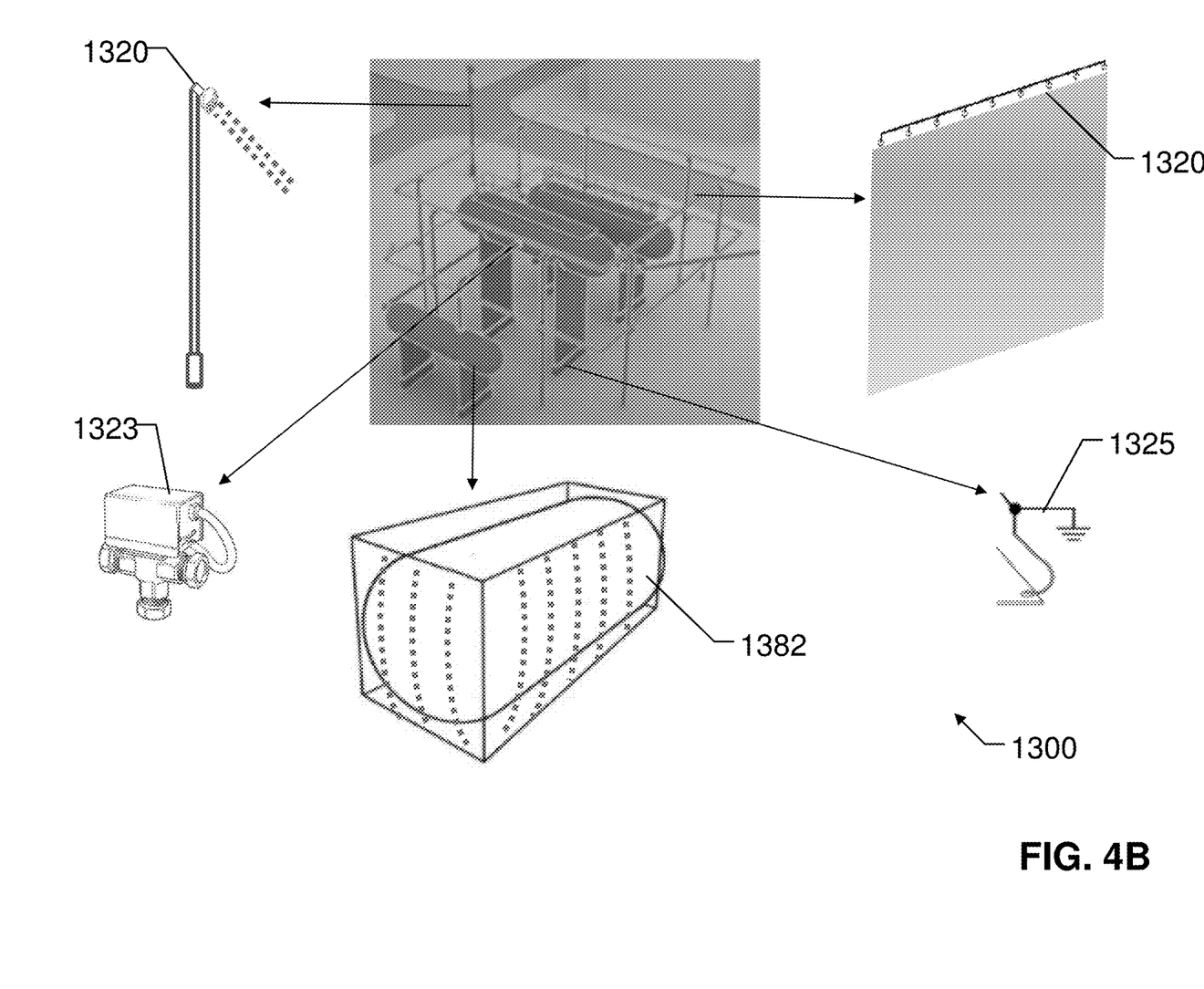

FIG. 4A schematically illustrates another exemplary chemical release detection system according to some embodiments of this disclosure, and FIG. 4B schematically illustrates some exemplary mitigation devices 1300. The mitigation devices 1300 may be devices capable of preventing the spread of and containing the released chemical, including, without limitation, a sprinkler or water curtain 1320, a water monitor/water cannon 1340, a combination of water cannons and sprinklers, emergency isolation valves 1323, electrostatic discharge (ESD) devices 1325, HVAC isolation devices, and Rapid Acid Transfer/Dump (RAT/RAD) systems (or Acid Evacuation System (AES)) to transfer the flammable/toxic chemicals from a leaking tank and/or equipment to a stand-by tank or in a separately secured tank 1382.

The image processor 1140 of the chemical release detection system 1000 may be configured to generate a signal to select and aim at a targeted area, and operate the water mitigation devices such as, for example, cannons/sprinkler system for HF and ammonia releases. The image processor 1140 may also be configured to generate a signal to activate other shutdown/mitigation devices such as, for example, a Rapid Acid Transfer device 1380 for HF alkylation processes. The Rapid Acid Transfer/Dump (RAT/RAD) system 1380 includes valves and piping and is configured to transfer a large volume of the flammable/toxic chemicals from a leaking tank and/or equipment to a stand-by tank or a separately secured tank 1382, as shown in FIG. 4B. In some embodiments, the RAT/RAD system includes its own deluge systems. In some embodiments, the mitigation devices 1300 may include pneumatic lines configured to transport neutralizing chemicals that neutralize flammable/toxic gases in the detected area.

As shown in FIGS. 4A and 4B, in some embodiments, the image processor 1140 is hardwired or wirelessly connected to the control room 1250. Further, the image processor 1140 may utilize a software program or application that is run by any computing device from any location or multiple locations. For example, this allows the chemical release detection system 1000 to be managed from a remote location.

The chemical release detection system 1000 may be controlled by a graphical user interface (GUI). The chemical release detection system 1000 may be configured to include an easy-to-understand graphical user interface that shows the cloud overlay on a plot plan. The graphical user interface may be configured to change the views of the camera. The graphical user interface may also include the capability to setup different camera interfaces. The graphical user interface may further be configured to setup different detector inputs. The graphical user interface may include the capability to view the video of the release from up to 5 minutes before the start of release until the release stops in some embodiments. The graphical user interface may display alarms when the release is detected and verified by the plurality of visual range cameras 1120.

The graphical user interface may also serve as a diagnostic control for the operator of the chemical release detection system 1000. The graphical user interface may include buttons for manual control, including start, stop, and emergency stop; statistical information collected; data analysis; and emergency response information. The graphical user interface may also include screens that show the estimated amount of released chemical, and the speed and direction of the chemical release. The graphical user interface may be located in any appropriate location in communication with the chemical release detection system 1000 and related process lines. In an embodiment, the graphical user interface is hard wired or wirelessly connected to the chemical release detection system 1000. In some embodiments, one or more graphical user interfaces may be remotely located from the chemical release detection system 1000. The graphical user interface may be part of or in direct communication with the image processor 1140. For example, the graphical user interface may be included in the image processor 1140 such as a software program or application. The graphical user interface may allow a user to operate the system remotely. The graphical user interface may be included in a remote computing device, e.g., a desktop computer, laptop, notebook, tablet, smartphone or the like. In some embodiments, any of the afore-mentioned devices are utilized in conjunction with the graphical user interface. The remote computing device may communicate directly with the graphical user interface. The remote computing device may act as a surrogate device for the graphical user interface. In these embodiments, a duplicate of the graphical user interface may be displayed on the remote computing device. In some embodiments, the graphical user interface may be in communication with user's data monitoring system such as, for example, a distributed control system (DCS) and a supervisory control and data acquisition (SCADA). This allows a user to utilize the remote computing device in conjunction with the graphical user interface. This also allows for remote operation of the present system 1000.

Figure 5:
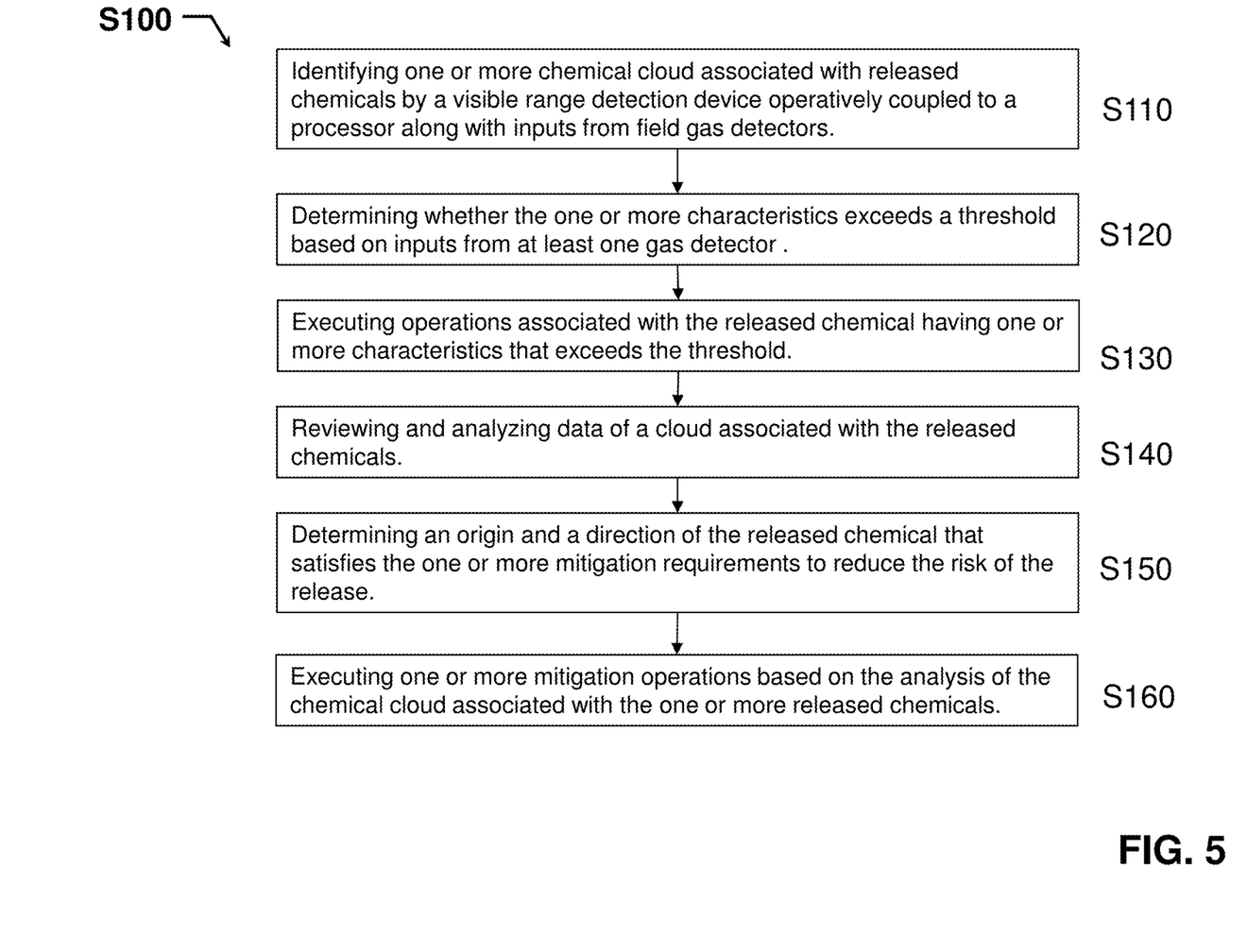
FIG. 5 shows a chemical release detection method according to an embodiment of the disclosure.

FIG. 5 illustrates a flow diagram of a non-limiting method S100 that analyzes a chemical release to determine one or more mitigation actions to reduce the risk of the release in accordance with one or more embodiments described herein. Repetitive description of like elements employed in other embodiments described herein is omitted for sake of brevity. In some embodiments, the method is a computer-implemented method. At S110, a chemical release detection system 1000 comprising a processor identifies one or more characteristics of chemical cloud 1227 associated with a released chemical by a chemical release detection device operatively coupled to a processor. At S120, the chemical release detection system 1000 determines whether the one or more characteristics exceeds a threshold based on inputs from at least one gas detector. At S130, the chemical release detection system 1000 executes operations associated with the released chemical having one or more characteristics that exceeds the threshold. At S140, the chemical release detection system 1000 analyzes the data of a cloud 1227 associated with the released chemical. The data analyzed includes the size of the cloud, orientation of the cloud 1227, and origin of the cloud 1227, etc. At S150, the chemical release detection system 1000 determines an origin and a direction of the released chemical that satisfies the one or more mitigation requirements to reduce the risk of the release. At S160, the chemical release detection system 1000 executes one or more mitigation operations based on the analysis of the chemical cloud 1227 associated with the one or more released chemicals.

Figure 6:
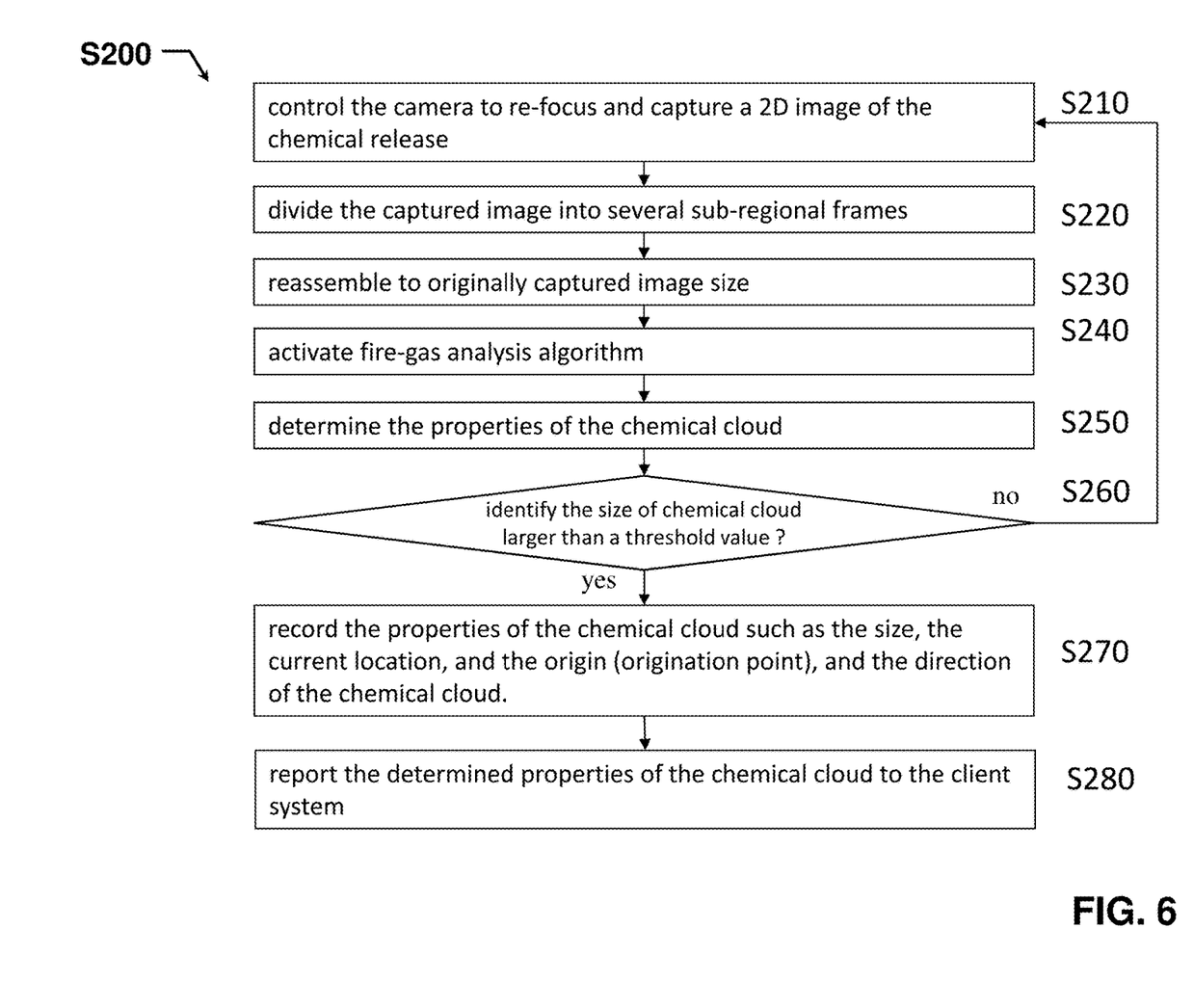
FIG. 6 illustrates a flow-chart of a method of analyzing the chemical release and communicates to the client system regarding the chemical release in accordance with one or more embodiments described herein.

FIG. 6 illustrates a flow diagram of a non-limiting method S200 that analyzes the chemical release and communicates to the client system regarding the chemical release in accordance with one or more embodiments described herein. In some embodiments, the method is a computer-implemented method. The image processor of the chemical release detection system analyzes the image from the camera at the client domain on-line. In operation, when the chemical release is detected by the chemical release detection system, at S210, the chemical release detection system controls the camera to re-focus and capture a 2D image of the chemical release that allows identifying one or more characteristics of chemical cloud 1227 associated with a released chemical. The chemical release detection system is operated by a chemical release detection device operatively coupled to a processor.

The image processor then, at S220, divides the captured images into several sub-regional frames to transmit the captured images to the image processor. In some embodiments, the captured images are divided equally in 2D space. In some embodiments, the captured images are divided proportionally-scaled in 2D space to provide enhancements to the images taken, such as post processing of the image. At S230, the received sub-regional frames are reassembled to the originally captured image size, so that the entire field of view can be analyzed by the image processor. At S240, a fire-gas analysis algorithm is activated. At S250, the fire-gas analysis algorithm then determines the properties of the chemical cloud 1227 such as size, current location, and an origin (origination point), and direction of the chemical cloud 1227 based on the one or more characteristics of chemical cloud associated with a released chemical. In some embodiments, two or more chemical clouds 1227 from different released chemicals can be received and analyzed simultaneously. At, S260, using the image processor, the size of chemical cloud 1227 identified by the captured image that are larger than initially determined threshold value are determined. Subsequently, at S270, the image processor 1140 records the properties of the chemical cloud 1227, such as the size, the current location, and the origin (origination point), and the direction of the chemical cloud 1227. Then, at S280, the image processor communicates and reports the determined properties of the chemical cloud to the client system.

In some embodiments, the image processor 1140 is further configured to control the two or more cameras to capture a 3D image of the chemical release to enhance identifying one or more characteristics of chemical cloud 1227 associated with a released chemical. In such embodiments, the image processor 1140 is further configured to provide a 3D direction that the chemical release is spreading in the chemical processing plant.

In some embodiments, the image processor 1140 is further configured to identify false input signals based on attenuation and lighting within the chemical processing plant so that the image processor avoids remediation operations associated with a chemical release determination based on the false input signals. In some embodiments, electrochemical gas sensors or infrared gas detectors are used to verify the absence of a flammable/toxic gas release, and confirm the false input signals.

In some embodiments, the image processor 1140 is further configured to identify whether the chemical cloud of the captured image is within a specific region of the plant. For example, if a distance to the chemical cloud 1227 identified by the captured image is greater than an upper threshold value the image processor reports the current location and the origin to the client system, and stops remediation operations for the chemical cloud in the reported pre-defined region of chemical processing plant. In some embodiments, the chemical release detection system 1000 includes a laser to measure the distance to the chemical release and to measure the speed of the chemical release cloud 1227. In some embodiments, the laser is a laser rangefinder or a laser device.

In some embodiments, the image processor 1140 is further configured to consider the emergency response team's location in the chemical processing plant. For example, the image processor can identify a human face 1402 or the color or patterns of clothing or equipment 1404 of the emergency response team processing such as by facial recognition or color or pattern identification. In such embodiments, the processor distinguishes between the emergency response team and the chemical cloud, and stops remediation operations in the vicinity of the emergency response team, so as to not subject the response team or other works to the remediation operations.

In some embodiments, the image processor 1140 is further configured to take the congestion of the chemical process lines into consideration. The congestion includes arrangements or structure of the chemical process line that can be included as parameters, so that the image processor 1140 may determine the priorities and type of remediation actions necessary such as, when and how (e.g. sequence) a water mitigation equipment needs to be activated or adjusted among chemical process line. In some embodiments, the image processor is further configured to take the weather and lighting conditions around the chemical process lines into consideration before implementing remediation efforts.

As previously discussed with reference to FIG. 3, some embodiments include electronic components, for example, microprocessors, storage, and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra-density optical discs, any other optical or magnetic media, and floppy disks. The computer-readable media can store a computer program that is executable by at least one processing unit and includes sets of instructions for performing various operations. Examples of computer programs or computer code including machine code, for example, produced by a compiler, and files including higher-level code that are executed by a computer, an electronic component, or a microprocessor using an interpreter.

While the above discussion primarily refers to microprocessor or multi-core processors that execute software, some embodiments are performed by one or more integrated circuits, for example, application specific integrated circuits (ASICs) or field programmable gate arrays (FPGAs). In some embodiments, such integrated circuits execute instructions that are stored on the circuit itself.

To provide for interaction with a user, implementations of the subject matter described in this specification can be implemented on a computer having a display device, e.g., a CRT or LCD monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

An embodiment of the disclosure is a chemical release detection system that comprises a camera, an output control member, a mitigation member, and a controller. The camera is configured to detect a release of chemical and operatively in communication with at least one gas detector for a chemical of interest. The output control member is configured to generate commands. The mitigation member configured to reduce risk generated by the released chemical based on the commands by the output control member. The controller is in operative communication with the camera, the output control member, and the mitigation member configured to notify a user of the release of the chemical, and provide an origin of the release and a direction of the release. In such embodiments, the controller controls the operation of the output control member and the mitigation member.

In some embodiments, the output control member comprises at least one programmable control logic device in communication with the controller. In some embodiments, the output control member receives a signal from line/point detectors. In some embodiments, the mitigation member comprises at least one selected from the group consisting of a water curtain; a water monitor; a water cannon; a sprinkler; heating, ventilation, an HVAC isolation device; electrostatic shock dissipation device; and an acid dump. In some embodiments, the controller comprises one or more cloud detection algorithms. In some embodiments, the chemical release detection system further comprises a display, in which the controller communicates with the display. In some embodiments, the display is a video display. In other embodiments, the camera is a video camera. In some embodiments, the controller is in wired or wireless communication with the camera, an isolation member, and the mitigation member. In some embodiments, the chemical release detection system includes a gas detector In some embodiments, the controller is configured to detect the chemical release. The controller is configured to identify one or more characteristics of the released chemical. Then, the controller determines whether the characteristics exceed a threshold value. The controller is also configured to execute remediation operations associated with the chemical when the identified characteristic detected exceeds the threshold value. The controller is configured to determine a location of the chemical and a direction in which the chemical is spreading is heading. Then the controller executes one or more mitigation operations based on a data analysis of the chemical release.

Another embodiment of the disclosure is a method. The method comprises detecting a chemical release. Subsequently, one or more characteristics of the released chemical is identified. Then, whether the characteristics exceeds a threshold value is determined. When the identified characteristic detected exceeds the threshold value, remediation operations associated with the chemical is executed. Subsequently, a location of the chemical and a direction in which the chemical release is heading are determined. Then, based on a data analysis of the chemical release, one or more remediation operations are executed.

In some embodiments, the chemical release is detected by one or more cameras. In some embodiments, the one or more cameras are visual range cameras. In some embodiments, two or more cameras are controlled to capture a 3D image of the released chemical to provide a 3D direction of the released chemical. In some embodiments, after executing the remediation operations, the remediation operations are analyzed. In some embodiments, the identifying the one or more characteristics of the released chemical, includes a chemical composition of a cloud of the released chemical, a size of the cloud, an orientation of the cloud, and an origin of the cloud. In some embodiments, based on the false input signals, false input signals are identified to avoid remediation operations associated with a chemical release determination. In some embodiments, whether a cloud of the released chemical is outside a boundary is determined, and then, when the cloud is outside the boundary, the remediation operations are stopped. In some embodiments, a human face or items of an emergency response team are identified, and then, remediation operations are stopped in a region where humans are present. In some embodiments, the one or more identified characteristics of the released chemical include the chemical composition of the released gas.

The foregoing outlines features of several embodiments or examples so that those skilled in the art may better understand the embodiments of the present disclosure. Those skilled in the art should appreciate that they may readily use the present disclosure as a basis for designing or modifying other processes and structures for carrying out the same purposes and/or achieving the same advantages of the embodiments or examples introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method, comprising:
   detecting a gas cloud of a chemical release by a camera;
   identifying characteristics of the gas cloud of the released chemical that include a size of the gas cloud, an orientation of the gas cloud, and an origin of the gas cloud;
   determining whether the characteristics exceed a threshold value;
   executing remediation operations associated with the chemical when the identified characteristic detected exceeds the threshold value;
   determining a location of the chemical and a direction in which the chemical release is heading; and
   executing one or more remediation operations based on a data analysis of the chemical release.

2. The method of claim 1, further comprising:
   analyzing the remediation operations after executing the remediation operations.

3. The method of claim 1, further comprising:
   identifying false input signals to avoid remediation operations associated with a chemical release determination based on the false input signals.

4. The method of claim 1, further comprising:
   determining whether a cloud of the released chemical is outside a boundary; and stopping the remediation operations when the cloud is outside the boundary.

5. The method of claim 1, further comprising identifying a chemical composition of the gas cloud of the released chemical.

6. The method of claim 1, wherein the chemical release is detected by one or more cameras.

7. The method of claim 6, wherein the one or more cameras are visual range cameras.

8. The method of claim 7, wherein two or more cameras are controlled to capture a 3D image of the released chemical to provide a 3D direction of the released chemical.

9. A method, comprising:
   detecting a chemical release;
   identifying one or more characteristics of the released chemical;
   determining whether the characteristics exceed a threshold value;
   executing remediation operations associated with the chemical when the identified characteristic detected exceeds the threshold value;
   determining a location of the chemical and a direction in which the chemical release is heading;
   executing one or more remediation operations based on a data analysis of the chemical release;
   identifying a human face or items of an emergency response team; and stopping remediation operations in a region where humans are present.

* * * * *

UNITED STATES PATENT AND TRADEMARK OFFICE
CERTIFICATE OF CORRECTION

PATENT NO. : 11,636,750 B2
APPLICATION NO. : 17/062466
DATED : April 25, 2023
INVENTOR(S) : Jatin Navin Shah et al.

It is certified that error appears in the above-identified patent and that said Letters Patent is hereby corrected as shown below:

In the Specification

Column 4, Lines 55 - 67, Column 5, Lines 1 - 22, should read:
The one or more cloud detection algorithms 1144 are configured to monitor and detect the origin and the direction of the release for the gas cloud 1227, including the chemical composition, the size, shape, or other characteristics of the flammable/toxic gas to determine an appropriate safety response. The software program may, by way of a non-limiting example, analyze pixel patterns using these programmed algorithms 1144 to check for the released chemical. This feature is particularly useful to determine when, and from where, the chemical release originated from. Additionally, the software program may serve to provide an enlarged visual representation of the chemical in question for analysis of the direction of the cloud 1227 of released gas. The one or more cloud detection algorithms 1144 may further aid in the photographing of the flammable/toxic gas, enhancement of the image such as contrasting the area of the flammable/toxic gas. This provides a more accurate image of the released chemical and the released area/location in some embodiments. The one or more cloud detection algorithms 1144 may include any appropriate light source, including, but not limited to, a dark field ring light, a black light, an incandescent light bulb, LED, etc. Further, any image enhancing device may be utilized with the present disclosure. The chemical release detection system 1000 may also contemplate a computing device and/or software program that provides enhancements to the images taken, such as post processing of the image. In some embodiments, the images are not enhanced, i.e. the plurality of visual range cameras 1120 have a sufficient resolution that such enhancements are not necessary. In other embodiments, an image enhancement, such as those described herein, are utilized on all of the images, some of the images (such as ones that exceed a specific threshold), or on a random or select number of the images.

Signed and Sealed this
Third Day of October, 2023

Katherine Kelly Vidal
*Director of the United States Patent and Trademark Office*